United States Patent [19]

Sacharoff et al.

[11] Patent Number: 5,395,362
[45] Date of Patent: Mar. 7, 1995

[54] METHODS AND APPARATUS FOR DISTRIBUTING LASER RADIATION

[75] Inventors: Alex G. Sacharoff, Framingham; David W. Haluska, Newton, both of Mass.

[73] Assignee: Summit Technology, Waltham, Mass.

[21] Appl. No.: 821,747

[22] Filed: Jan. 14, 1992

[51] Int. Cl.$^6$ ............................................. A61B 17/36
[52] U.S. Cl. ...................................... 606/17; 606/13; 128/6; 604/20; 607/89
[58] Field of Search .................. 606/7, 10, 13–17; 128/6, 398; 604/20, 21, 19; 385/47, 50, 53–56, 59, 66, 67, 70, 73, 13; 607/89, 88

[56] References Cited

U.S. PATENT DOCUMENTS

| | | | |
|---|---|---|---|
| 3,455,625 | 7/1969 | Brumley et al. | 385/54 |
| 3,834,391 | 9/1974 | Block | 128/398 |
| 3,901,581 | 8/1975 | Thiel | 350/96 |
| 3,910,678 | 10/1975 | McCartney et al. | 350/96 |
| 4,383,729 | 5/1983 | Suzuki et al. | 606/16 |
| 4,423,923 | 1/1984 | Frazier et al. | 385/55 |
| 4,433,896 | 2/1984 | Frazier | 385/56 |
| 4,482,214 | 11/1984 | Hill et al. | |
| 4,551,628 | 11/1985 | Grossman | 250/503 |
| 4,657,014 | 4/1987 | Edelman et al. | |
| 4,657,169 | 4/1987 | Dostoomian et al. | 228/103 |
| 4,686,979 | 8/1987 | Gruen et al. | |
| 4,718,416 | 1/1988 | Nanaumi | |
| 4,732,448 | 3/1988 | Goldenberg | 604/21 |
| 4,733,944 | 3/1988 | Fahlen et al. | |
| 4,824,204 | 4/1989 | Pafford | 385/73 |
| 4,832,023 | 5/1989 | Murphy-Chutorian et al. | 604/96 |
| 4,842,360 | 6/1989 | Caro et al. | |
| 4,848,336 | 7/1989 | Fox et al. | |
| 4,862,886 | 9/1989 | Clarke et al. | |
| 4,913,508 | 4/1990 | Blyler, Jr. et al. | 385/50 |
| 4,917,084 | 4/1990 | Sinofsky | 128/398 |
| 4,963,142 | 10/1990 | Loertscher | 606/14 |
| 4,978,186 | 12/1990 | Mori | 606/16 |
| 4,995,686 | 2/1991 | Blonder et al. | 385/50 |
| 5,029,588 | 7/1991 | Yock et al. | 606/18 |
| 5,044,717 | 9/1991 | Levatter et al. | 385/33 |
| 5,188,632 | 2/1993 | Goldenberg | 606/17 |

FOREIGN PATENT DOCUMENTS

| | | |
|---|---|---|
| 0274205 | 7/1988 | European Pat. Off. |
| 0280414 | 8/1988 | European Pat. Off. |
| 3509421 | 9/1985 | Germany |
| 62-216216 | 9/1987 | Japan |
| 63-222385 | 12/1990 | Japan |
| 2116742 | 9/1983 | United Kingdom |
| 2180363 | 3/1987 | United Kingdom |
| 2228344 | 8/1990 | United Kingdom ......... 606/4 |
| WO91/04829 | 4/1991 | WIPO |

OTHER PUBLICATIONS

Grojean et al. (1980) Rev. Sci. Instrum. 51/3:375–376 "Production of Flat Top Beam Profiles for High Energy Lasers".

Simmons et al. (1974) Applied Optics 13/7:1629–1632 "Optical Beam Shaping Devices Using Polarization Effects".

Cullis et al. (1979) The Instit of Physics "A Device for Laser Bean Diffusion and Homogenisation".

Han et al. (1983) Applied Optics 22/22:3644–3647 "Reshaping Collimated Laser Beams with Gaussian Profile to Uniform Profiles".

Deng et al. (1986) Applied Optics 25/3:377–381 "Uniform Illumination of Large Targets Using a Lens Array".

Ozaki et al. (1989) Applied Optics 28/1:106–110 "Cylindrical Fly's Eye Lens for Intensity Redistribution of an Excimer Laser Beam".

Primary Examiner—Stephen C. Pellegrino
Assistant Examiner—Jeffrey A. Schmidt
Attorney, Agent, or Firm—Thomas J. Engellenner

[57] ABSTRACT

Apparatus and methods are disclosed for distributing and delivering laser radiation with substantially uniform intensity to multi-spatial locations. Laser radiation is directed into a fiber optic waveguide which homogenizes the spatial intensity of the laser beam via mode-mixing. The laser radiation is then coupled from the mode-mixing waveguide to multiple distribution fibers that are terminated at desired spatial locations, e.g., at the distal end of a surgical tool. The output from each of the multiple distribution fibers is laser radiation of substantially uniform intensity.

5 Claims, 4 Drawing Sheets

METHODS AND APPARATUS FOR DISTRIBUTING LASER RADIATION

BACKGROUND OF THE INVENTION

This invention relates generally to laser therapy and, in particular, methods and apparatus for conditioning a laser beam for distribution to a therapy site.

Laser radiation emitted from the confines of a laser cavity is typically non-uniform in intensity. Most commonly, lasers exhibit Gaussian intensity profiles across at least one axis in the so-called $TEM_{oo}$ mode of operation. Many profiles are possible, however, and depend upon a variety of factors, including the laser cavity geometry and alignment.

Non-uniformity in a laser beam profile often can pose problems, particularly in laser therapy applications. Irradiation of human tissue during surgery or therapy usually requires precise control of exposure time and power. When a therapeutic laser is coupled with a multi-fiber surgical tool, e.g., a catheter carrying a plurality of optical fibers, the problem of non-uniformity can become pronounced because the inhomogeniety in the laser beam's spatial intensity is transferred directly to the fibers within the tool. In regions of lower intensity, e.g., toward the edges of the therapeutic laser beam, the receiving fiber typically will transmit radiation of a lower intensity. Near the optical axis of the laser beam, the receiving fiber will typically transmit radiation of a higher intensity.

Consequently, the laser power delivered at the distal end of a multi-fiber surgical tool and equivalently at the target tissue region, can be very difficult to control. When a plurality of laser fibers are used to deliver radiation to a target region, the intensity of radiation delivered by each fiber can vary widely.

Methods do exist to homogenize the intensity profiles of lasers, but they are often inefficient. For example, high energy lasers are sometimes put through a process known as "beam-scraping." This process approximates a spatially-uniform, laser beam intensity by allowing the beam to expand and then blocking off (e.g., with an aperture or diaphragm) regions of lower intensity. After one or more passes through a beam-scraping system, the laser beam is clipped to provide a top hat-like profile.

However, this is wasteful since a substantial amount of energy is dissipated during beam scraping operations. It is also generally not desirable for systems in which therapeutic laser radiation must be transmitted via optical fibers. In such cases, intensity control is desired without significant energy loss.

It is, accordingly, an object of this invention to provide apparatus and methods for uniformly transferring laser radiation from a source to a plurality of optical fibers without substantial loses in energy.

It is another object of this invention to provide apparatus and methods for delivering laser radiation to surgical tools.

Yet another object of this invention is to provide apparatus and methods to enable greater precision and control in laser surgical instruments and applications.

These and other objects of the invention are evident in the description that follows.

SUMMARY OF THE INVENTION

Laser radiation for surgical and therapeutic purposes can be efficiently delivered via optical fibers by first directing the radiation into a mode-mixing waveguide, e.g., a single core fiber, which mixes the transmitting modes of the laser radiation. The mode-mixing provided by the single core fiber or similar waveguide homogenizes the spatial intensity distribution of the transmitted laser beam. This modified laser beam is in turn coupled to one or more fibers, in optical alignment with the mode-mixing waveguide, thereby transmitting and distributing substantially uniform intensities of radiation through each of the receiving fibers.

In another aspect of the invention, the juncture between the mode-mixing waveguide and the one or more distribution fibers can include the addition of an optical coupling means to reduce reflection losses which occur at optical interfaces. The juncture created by the single core fiber and the multiple fibers can thus include an index matching fluid or an evacuated chamber.

According to yet another aspect of the invention, the multiple fibers can be disposed within a surgical tool and arranged in a predefined pattern. For example, the therapeutic laser radiation can be delivered in a circular or annular pattern of a selected radius. If the therapy is ablative surgery, the array of laser-emitting fibers can provide a cutting diameter which is greater than the size of the single core fiber, and the laser radiation delivered by each of the multiple fibers will be of approximately uniform intensity, thereby simplifying process controls.

Another aspect of the invention provides that the coupling between the single core fiber or other mode-mixing waveguide and the multiple distribution fibers of the surgical tool readily be engaged and disengaged at the juncture. Thus, several different surgical tools easily can be interchanged to provide different laser delivery options for therapeutic surgery.

In a further aspect of the invention, apparatus and methods are provided for selectively distributing laser radiation to less than all of the receiving fibers so as to vary the irradiation pattern at the surgical or other laser therapy site.

The advantages presented by the features and aspects of the invention are several. The spatial intensity profile of a laser beam is modified to provide a nearly uniform intensity distribution between receiving fibers. Thus, applications requiring multiple laser delivery points, together with uniform intensities, are particularly suited for the invention described herein. Laser surgery applications further benefit according to the invention by the laser delivery options available via use of different or adjustable surgical tools (e.g., instruments having different focal depths or variable fiber array patterns).

The invention will next be described in connection with certain preferred embodiments. However, it should be clear that various additions, subtractions and modifications can be made by those skilled in the art without departing from the scope of the invention. The invention will find application in various fields of surgery, such as conventional surgical procedures employing laser scalpels and the like, as well as alternative procedures in which laser radiation is delivered via catheters, arthroscopes, endoscopes or other surgical tools to perform angioplasty, arthroplasty, excisions, dental surgery or equivalent procedures.

BRIEF DESCRIPTION OF THE DRAWINGS

A more complete understanding of the invention may be obtained by reference to the drawings in which.

DETAILED DESCRIPTION

Figure 1:
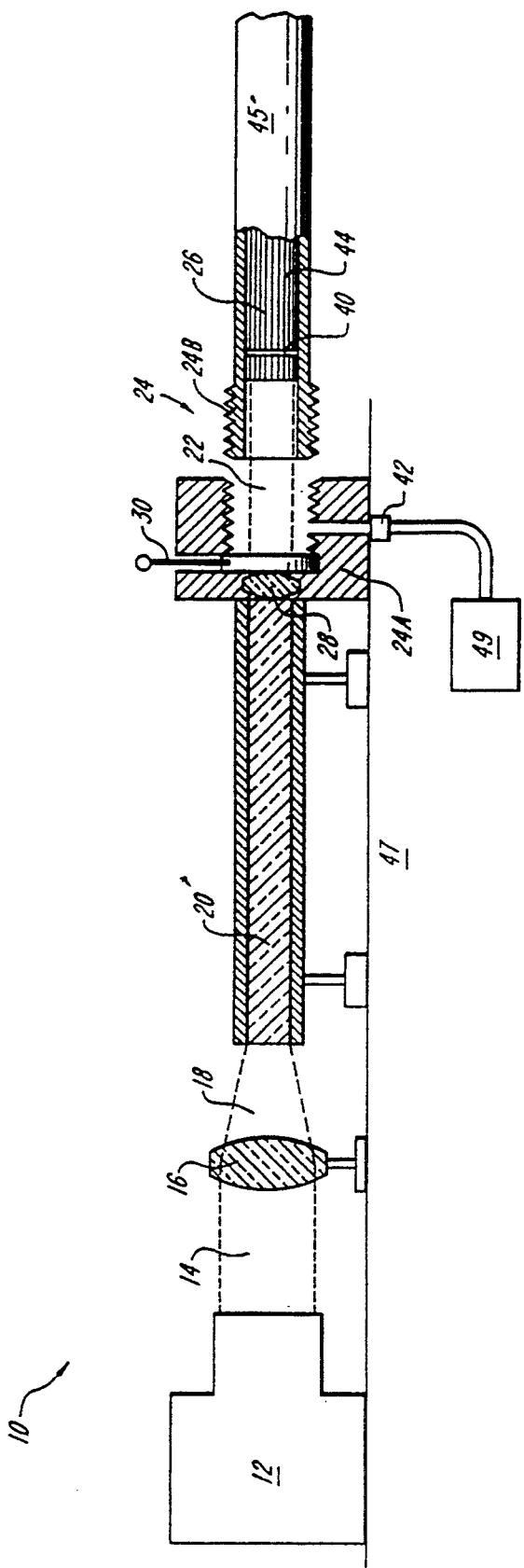
FIG. 1 is a partial cross-sectional, schematic side view of a laser delivery system according to the invention.

FIG. 1 illustrates a laser delivery system 10 according to the present invention, including laser 12, optical processing module 16, mode-mixing waveguide 20 and distribution fibers 26. In use, laser 12 produces a beam of radiation 14 having an inherent nonuniformity across at least one cross-sectional axis. The laser radiation 14 is processed in module 16 which will typically include focussing lenses and other optical elements to transform the beam into a desired cross-sectional area and/or shape. However, the output beam 18 of module 16 will continue to possess inhomogeneities in spatial intensity.

In the present invention, a mode-mixing waveguide, e.g., a single core optical fiber, 20 receives the focussed beam 18 and, through a process of randomization within the fiber 20, itself, produces a modified beam 22 that has a substantially uniform, cross-sectional intensity. This modified beam 22 is then coupled via interface 24 to provide uniform portions of the laser radiation to the distribution fibers 26.

By way of further explanation with reference to FIG. 1, the intensity profile of the radiation beam 14 leaving a laser 12 is typically non-uniform in the radial direction. If several fibers were to capture this intensity distribution for delivery to one or more locations, the intensity captured and delivered would be different among the several fibers.

In contrast, the output beam 22 of mode-mixing fiber 20 is substantially uniform in spatial intensity distribution. If several fibers 26 capture this beam 22, the receiving fibers 26 receive nearly equivalent intensity levels; and, therefore, the laser energy delivered by each of the multiple fibers 26 will be approximately uniform.

Figure 2:
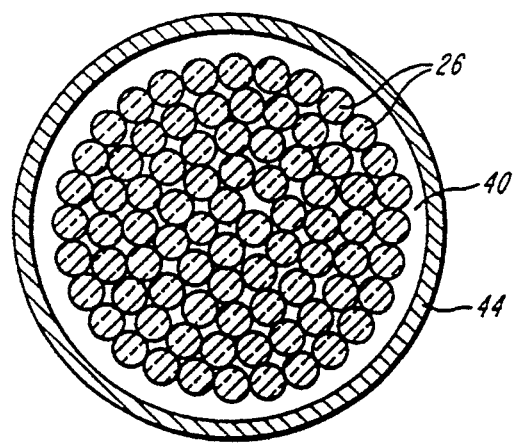
FIG. 2 is a schematic end view of the multi-fiber receptacle shown in FIG. 1.

As shown in FIG. 1, a plurality of distribution fibers can be bundled together at the proximal end of a surgical tool 45 and optically aligned with output beam 22 via receptacle 24. In the illustrated embodiment, receptacle 24 included a threaded cup element 24A, which is preferably mounted to the optical rail 47 or other fixed portion of the system chassis or housing, and a complementary threaded plug 24B at the proximal end of the surgical tool 45. As shown in both FIGS. 1 and 2, the bundle of distribution fibers 26 is preferably recessed within the mouth of receptacle plug 24B and secured in place inside a peripheral cable wall 44 by a mounting means 40 (e.g., a plate with holes to secure each distribution fiber 26). The ends of the individual fibers can be heat treated prior to assembly to provide additional resistance to laser damage when the surgical tool 45 is intended to transmit high peak power radiation.

When the receptacle cup and plug 24A and 24B are mated, the distribution fibers 26 are optically aligned, such that the output beam 22 of the mode-mixing fiber 20 is transmitted directly and with substantially the same intensity to the individual fibers of the array. Receptacle 24 can further include a passageway or valve 42 for connection to an evacuation means and/or a fluid source 49, in order to create a vacuum within the receptacle 24 or to introduce a fluid medium and, thereby, reduce transmission/coupling losses.

Figure 3A:
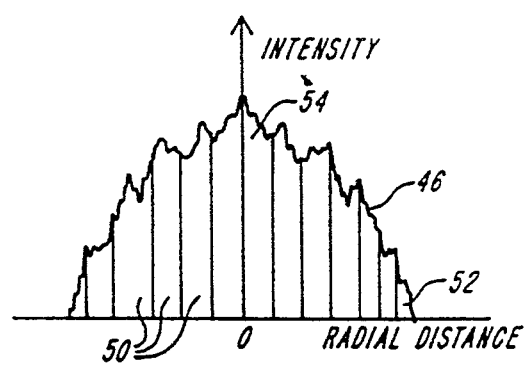
FIG. 3A is a schematic cross-sectional diagram of the laser beam intensity profile before modification by the single core fiber.
Figure 3B:
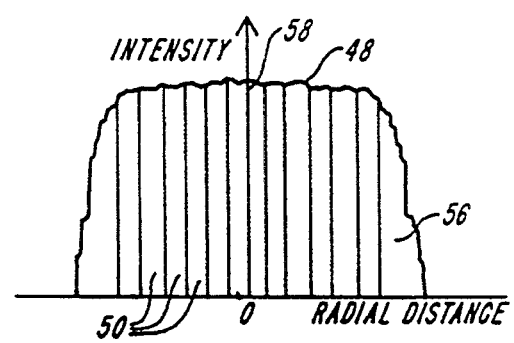
FIG. 3B is a schematic cross-sectional diagram of the laser beam intensity profile after modification by the single core fiber.

FIG. 3A and FIG. 3B illustrate the laser energy at two different locations along the optical path of FIG. 1. FIG. 3A depicts the laser beam intensity profile of the laser beam 18 exiting the optical processing means 16 but before its transmitted modes are mixed by the single core fiber 20 of FIG. 1. FIG. 3B depicts the laser beam intensity profile of the laser beam 22 after its transmitted modes are mixed by the single core fiber 20. The spatial position of several fibers are shown schematically by elements 50 within the intensity profiles curves 46 and 48. At the point of intersection, where these elements 50 meet, the intensity profile 48, the relative energy captured by the several fibers can be evaluated.

As shown in FIG. 3A, if several fibers are placed to capture the laser energy before the laser beam passes through a mode-mixing process, the fibers at the outer portions 52 of the beam will receive less energy than the fibers near the optical axis of the beam 54. This occurrence is significantly less pronounced in FIG. 3B. The fibers near the edge 56 of the laser beam exiting the single core fiber receive nearly the same energy as those fibers 58 near the laser beam optical axis. Therefore, the laser delivery by the fibers in FIG. 3B is significantly more uniform than the laser delivery by the fibers in FIG. 3A.

With reference again to FIG. 1, laser energy 18 coupled into the fiber 20 undergoes a process of mode-mixing. Laser radiation may be efficiently distributed to the multiple fibers 26 with approximately uniform intensities by first coupling the radiation through the single-core, mode-mixing fiber 20. In some applications, it may also be preferable to provide a ramp or progressive increase in the laser radiation input prior to full power exposure in order to minimize the potential for damage to either the mode-mixing fiber 20 or the distribution fibers 26. Catheters, other surgical tools and devices which might benefit from redistributed uniform laser radiation can easily employ the invention for the desired application. In laser angioplasty, for instance, controlled delivery of pulsed laser radiation is desirable to limit the damage to tissues surrounding a particular target obstruction within the body. By homogenizing the laser beam, and by employing a multi-fiber, surgical tool, both the control of energies and the spatial delivery options applied to the particular target are greatly improved.

The invention relies upon mode-mixing fiber optics. Successful optical waveguides confine and transmit light energy in discrete modes. The mathematical physics of this phenomenon is quite complex, yet its functioning may be intuitively described by wave propagation and boundary conditions. The light waves within the fiber 20 are most conveniently represented by electrical field vectors describing the phase front to the laser beam. In order for energy to propagate through the fiber, these electric fields must reflect at the core/-cladding interface of the single core fiber 20. At the same time, any energy outside this interface must decay rapidly. Thus, one boundary condition is simply that the summation of electric field energy into the core/cladding interface must equal the sum of the reflected parts and the parts transmitted through the interface called evanescent waves.

The boundary conditions, however, are not just magnitude ratios. Each reflection induces a 180 degree phase change to the electric field. When solving the boundary conditions, a complex series of phase relations are simultaneously solved. The resulting solution set representing the transmitted energy through the fiber is clearly not a continuous function. There are discrete solutions to the conditions set forth above. Each integer solution can be called a mode, and each mode has a different electrical field profile fulfilling the solution. Because the intensity of the transmitted energy equals the squared modulus of the electric field, the different modes also mean different spatial intensity distributions within the fiber. The first mode, for instance, is an intensity distribution peaking at the fiber center. The second mode has two peaks, symmetrical about the center. The third mode has three peaks, and so on.

The summation of these modes can transform a spatially, non-uniform laser beam into a beam of approximately uniform intensity. Increasing the number of modes increases the uniformity. The number of modes transmitted through the fiber depends upon a number of parameters, well-known to those skilled in the art, including index differences between the core and cladding, the numerical aperture of the fiber and the focused f/number of the incident laser radiation and the fiber diameter.

In accordance with the invention, the laser intensity profile is modified during the transmission through a mode-mixing waveguide 20. In one embodiment, a single-core fiber having an inner diameter (I.D.) of approximately 100 to about 1000 μm (e.g., about 600 μm), manufactured from hydroxy-doped, fused silicon or the like, is employed to produce a mode-mixing waveguide capable of transmitting a radiation beam of nearly uniform, cross-sectional intensity, ultraviolet laser radiation, e.g., 308 nm. This can be efficiently coupled into multiple fibers, e.g., from about 10 to about 100 fibers with diameters ranging from about 25 to about 300 μm (I.D.), constructed from similar materials, which may be redistributed in any pattern at the distal end of the surgical tool. In a preferred embodiment, the pattern at the tool's end is an annular ring pattern with a diameter greater than the single core fiber 20.

The invention can be practiced with a wide variety of laser sources, including infrared, visible and ultraviolet radiation-generating lasers, limited only by the transmissivity and damage thresholds of the optical elements. The invention can also be used to homogenize the spatial intensity profiles of non-coherent sources and, most generally, is useful whenever a spatially-uniform intensity profile is desired in a light source. In practice, the surgical and therapeutic advantages of the present invention primarily are useful with high energy, rapidly pulsed lasers, such YAG and other rare earth-based solid state lasers, or excimer and other gas discharge lasers, operating with pulse durations in the 100 microsecond to 1 nanosecond range.

The interface between the single core fiber 20 and the multiple fibers 26 can comprise air, an optical index matching medium or a vacuum. When light energy strikes an interface which has a different index of refraction, part of the light energy is reflected, commonly referred to as Fresnel reflection. These Fresnel reflections account for a loss in energy for the transmitted laser beam. Various index matching media, including nitrogen, inert gases, vacuum conditions and other interfaces known in the art, can be employed.

Figure 4:
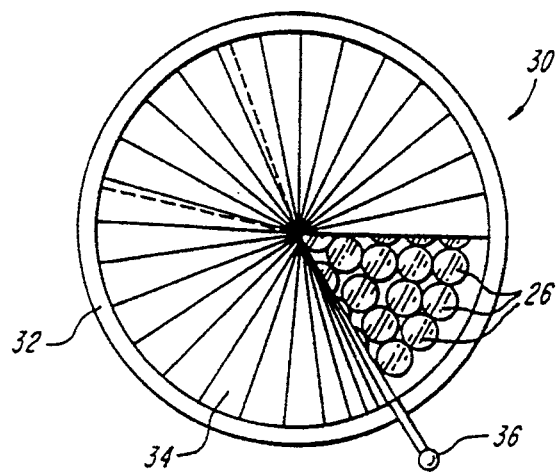
FIG. 4 is a schematic end view of the fiber selector shown in FIG. 1.

FIGS. 1 and 4 also illustrate a selection means 30 for selecting a limited subset of the distribution fibers 26 for transmission purposes. As shown in FIG. 1, element 30 is disposed with the optical path between the mode-mixing waveguide 20 and the distribution fibers 26. In one preferred embodiment, element 30 is removable. When disposed in the optical path element 30 can be adjusted to select certain distribution fibers 26. As illustrated in FIG. 4, element 30 includes an outer ring 32, a set of fan-like leaves 34 and an adjustment lever 36. By moving lever 36, the leaves 34 can be expanded or compressed to illuminate more or less of the fibers 26. The outer ring 32, preferably, can also rotate, such that any desired irradiation pattern at the distal end of the instrument can be accommodated. Other selection means, such as iris-like elements, electrooptic, or absorptive devices, can be substituted for the mechanism shown in FIG. 4.

Figure 5:
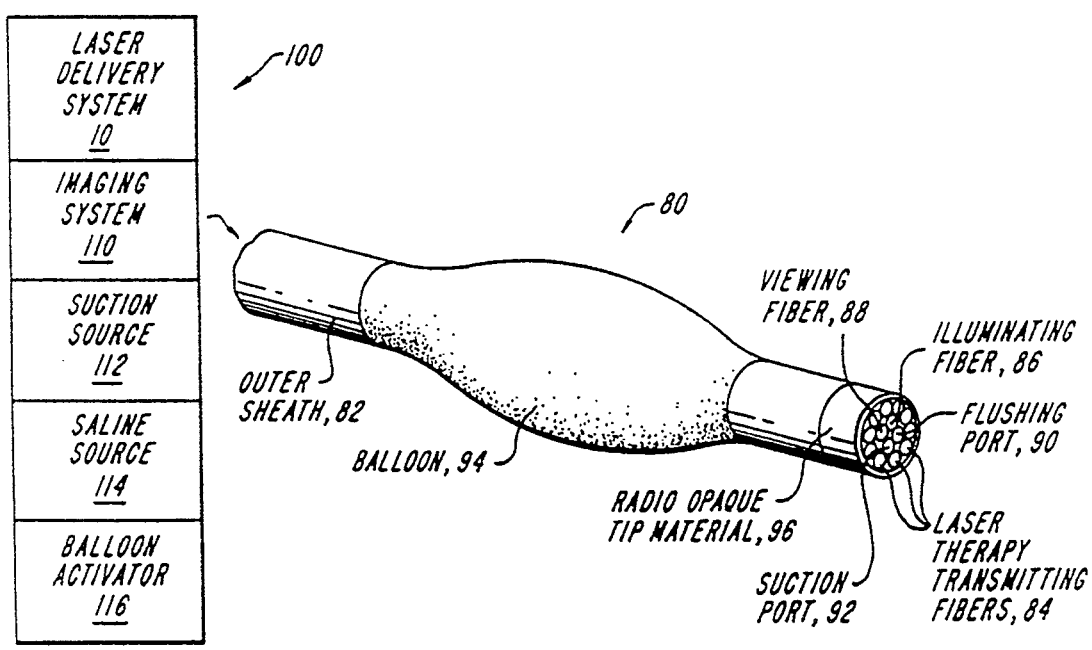
FIG. 5 is a schematic illustration of an angioplasty surgical tool for use in connection with the laser delivery system of FIG. 1.

FIG. 5 illustrates the distal end of a surgical tool 80 useful, for example, in angioplasty or endoscopy. In one embodiment, tool 80 is a catheter for performing angioplasty, including an outer sheath 82 carrying a plurality of laser radiation distribution fibers 84. As shown, the laser therapy transmitting fibers 84 are arranged in the catheter for disposition within a blood vessel, such that the fibers 84 can deliver ablative radiation to plaque or other lesions at an angioplasty site.

The catheter 80 of FIG. 5 can further include an imaging system comprising, for example, an illuminating fiber 86 and a viewing fiber 88 to permit visualization of the blood vessel or other body lumen. The catheter can further include a flushing port 90 and/or a suction port 92, for clearing blood and other materials from the field between irradiation fibers 84 and the target site. In some applications, the catheter 80 can further include a balloon structure 94 for temporarily obstructing blood-flow with the vessel, as well as a radio-opaque tip or marker 96 for extracorporeal imaging/locating of the catheter by X-ray photography.

In use, the catheter 80 is coupled to an overall surgi7 cal system 100 which includes the laser delivery system 10 of the present invention, as well as an imaging system 110 (e.g., an eye piece and/or video camera connected to the viewing of fiber 88), a suction source 11, a flushing fluid source 114 (e.g., saline or other fluids) an a balloon activator 116.

Figure 6A:
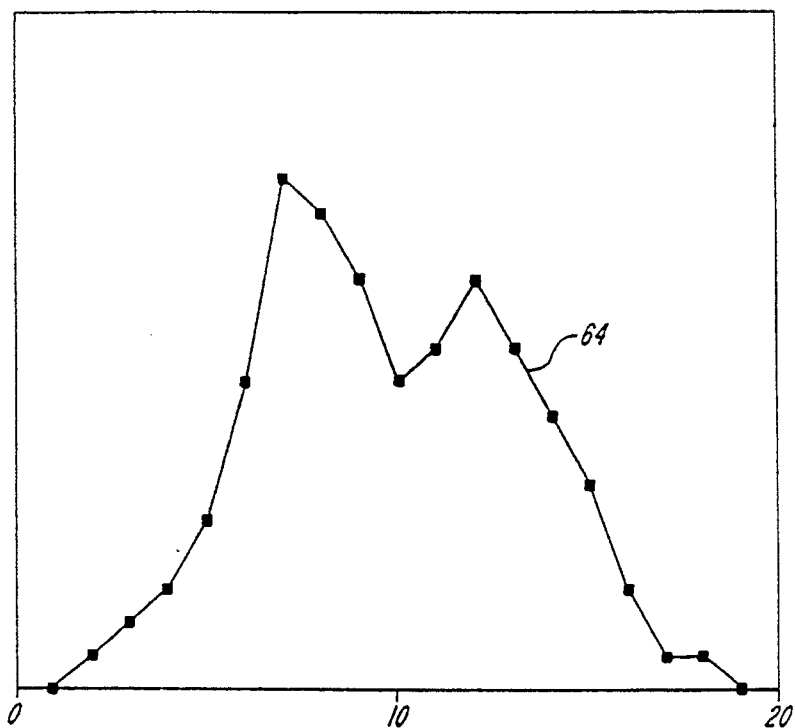
FIG. 6A is a graph of experimental data showing laser beam intensity versus cross-sectional location prior to beam modification by the invention.
Figure 6B:
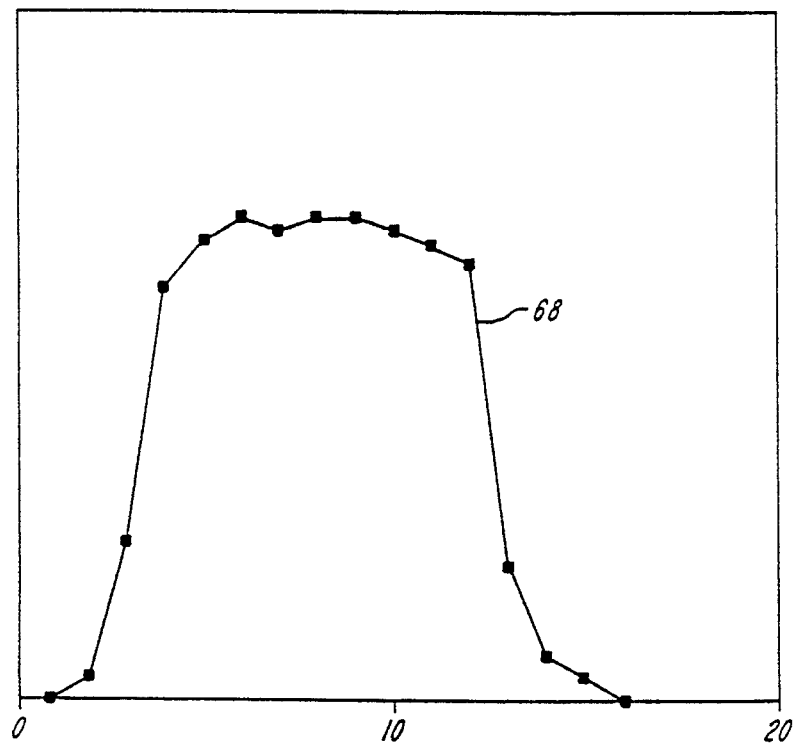
FIG. 6B is a graph of experimental data showing laser beam intensity versus cross-sectional location after modification by the invention.

FIGS. 6A and 6B provide experimental data showing the intensity modification by a single core fiber constructed in accordance with the invention. FIG. 6A shows an intensity profile 64 of a therapeutic excimer laser beam at the input to a single core, mode-mixing fiber. FIG. 6B shows an intensity profile 68 of the same therapeutic laser beam at the output of the single core, mode-mixing fiber. As seen in FIG. 6B, the intensity uniformity of the laser beam profile 68 after the mode-mixing process is significantly improved over the intensity profile 64 before the mode-mixing.

What is claimed is:

1. A method for delivering substantially uniformly intensity laser radiation to a plurality of spatial locations on a surgical tool, the method comprising:

directing laser radiation into a mode-mixing, single-core, fiber-optic waveguide;

coupling said therapeutic laser radiation from waveguide to multiple distribution fibers contained within a surgical tool;

terminating said multiple distribution fibers within the surgical tool at desired spatial locations; and selectively distributing radiation to a spatially discriminated subset of said distribution fibers to provide directional therapy changeable in the course of laser surgery.

2. The method of claim 1 wherein said step of directing the laser radiation into the mode-mixing waveguide further comprises the step of focusing the laser radiation into a region defined by the numerical aperture of said waveguide.

3. An apparatus for performing surgery by distributing laser radiation to multi7spatial locations, the apparatus comprising:

a single-core fiber, optically alignable with a source laser radiation and operating to mix the modes of said radiation as the radiation propagates through the single-core fiber;

focusing means for focusing laser radiation into said single-core fiber;

interface means, for transmitting said laser radiation from said single-core fiber to a plurality of distribution fibers contained within a surgical tool, such that the fluence of radiation transmitted to each distribution fiber is substantially uniform; and selection means for selectively distributing ablative radiation to a spatially discriminated subset of said distribution fibers to provide directional therapy changeable in the course of laser surgery.

4. The apparatus of claim 3 wherein the diameter of said single-core, mode-mixing fiber ranges from about 100 to about 1000 $\mu$m.

5. The apparatus of claim 3 wherein the diameter of distribution fibers ranges from about 25 to about 300 $\mu$m.

* * * * *